US00PP23854P2

(12) United States Plant Patent
Richards

(10) Patent No.: US PP23,854 P2
(45) Date of Patent: Aug. 27, 2013

(54) ***IBERIS* PLANT NAMED 'PINK ICE'**

(50) Latin Name: ***Iberis* hybrid**
Varietal Denomination: Pink Ice

(76) Inventor: Rodney W. Richards, Hereford (GB)

( * ) Notice: Subject to any disclaimer, the term of this patent is extended or adjusted under 35 U.S.C. 154(b) by 245 days.

(21) Appl. No.: 13/136,771

(22) Filed: Aug. 10, 2011

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — Penny J. Aguirre

(57) ABSTRACT

A new cultivar of *Iberis*, 'Pink Ice', characterized by its densely branched, compact plant habit, its late bloom period, its foliage that is dark green and glossy, its flowers that emerge from dark pink flower buds, open pale pink, and become darker pink as they mature and are consistent in size and color.

2 Drawing Sheets

Botanical classification: *Iberis* hybrid.
Variety denomination: 'Pink Ice'.

BACKGROUND OF THE INVENTION

The present invention relates to a new and distinct cultivar of *Iberis* plant, botanically of hybrid origin and known as *Iberis* 'Pink Ice' and will be referred to hereinafter by its cultivar name, 'Pink Ice'. The new cultivar represents a new cultivar of *Iberis*, an herbaceous perennial grown for landscape use.

'Pink Ice' was discovered by the Inventor in Hereford, United Kingdom in April 2009 in a trial bed containing the Inventor's collection of both unnamed and named varieties of *Iberis*. The parentage is not known, however it is likely that 'Pink Ice' is a hybrid between *Iberis sempervirens, Iberis gibraltarica*, or *Iberis aurosica* based on the characteristics of 'Pink Ice' and their proximity to the location where 'Pink Ice' was discovered.

Asexual reproduction of the new cultivar was first accomplished by the Inventor via stem cuttings in June 2009 in Hereford, Herefordshire, United Kingdom. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Pink Ice' as a unique cultivar of *Iberis*.

1. 'Pink Ice' exhibits, densely branched, compact plant habit.
2. 'Pink Ice' blooms later in the season than cultivars of *Iberis sempervirens* known to the Inventor.
3. 'Pink Ice' exhibits foliage that is dark green and glossy.
4. 'Pink Ice' exhibits flowers that emerge from dark pink flower buds, open pale pink, and become darker pink as they mature.
5. 'Pink Ice' exhibits flowers that are consistent in size and color.

'Pink Ice' can be compared to the most likely parent plants, plants of, *Iberis sempervirens, Iberis gibraltarica,* and *Iberis aurosica* in the Inventor's trial bed. Plants of *Iberis sempervirens* differ from 'Pink Ice' in having a less densely branched plant habit, in having white flowers, and in blooming earlier. Plants of *Iberis gibraltarica* differ from 'Pink Ice' in having flowers that are violet in color. Plants of *Iberis aurosica* differ from 'Pink Ice' in being shorter in height and in having flowers that are white in color and emerge from buds that are lilac in color. The closest comparison cultivar is *Iberis aurosica* 'Sweetheart' (not patented) which is similar to 'Pink Ice' in having pink flowers. 'Sweetheart' differs from 'Pink Ice' in being shorter in height, in being a seed strain, and in having flowers that emerge pink and change to lilac in color.

BRIEF DESCRIPTION OF THE DRAWING

The accompanying colored photographs illustrate the overall appearance and distinct characteristics of the new *Iberis*. The photographs were taken of a plant about 8 months in age as grown outdoors in a one-gallon container in Watsonville, Calif.

Figure 1:
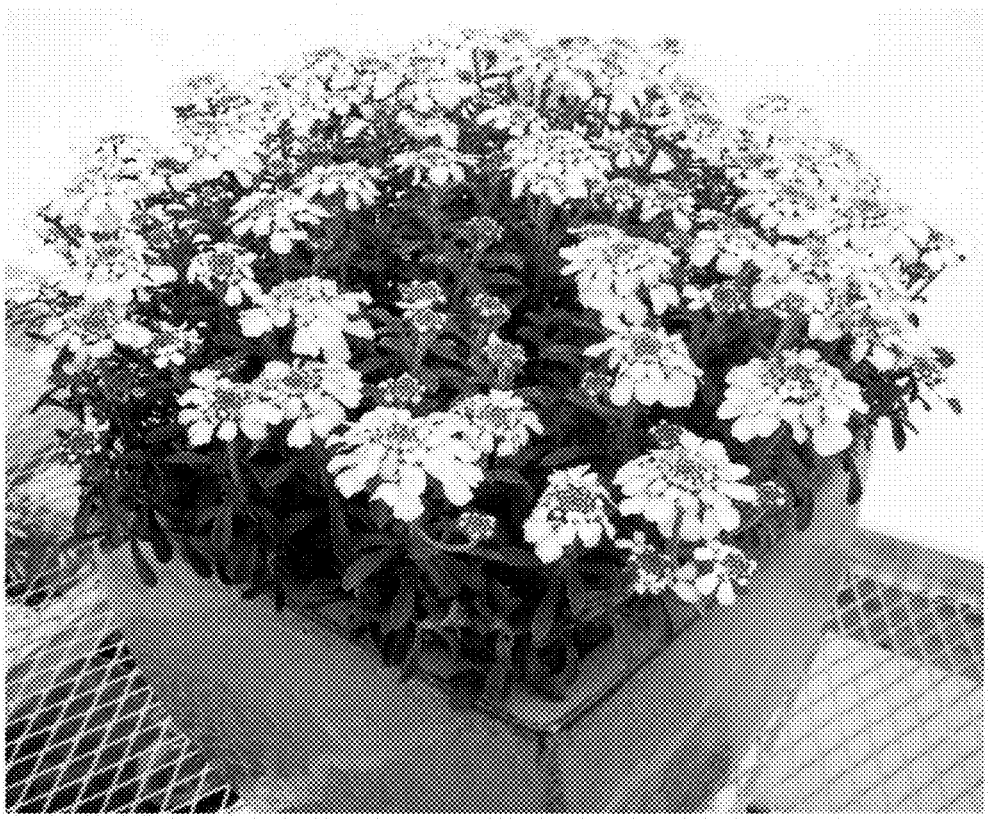
FIG. 1 provides a view of the plant habit of 'Pink Ice' in bloom.
Figure 2:
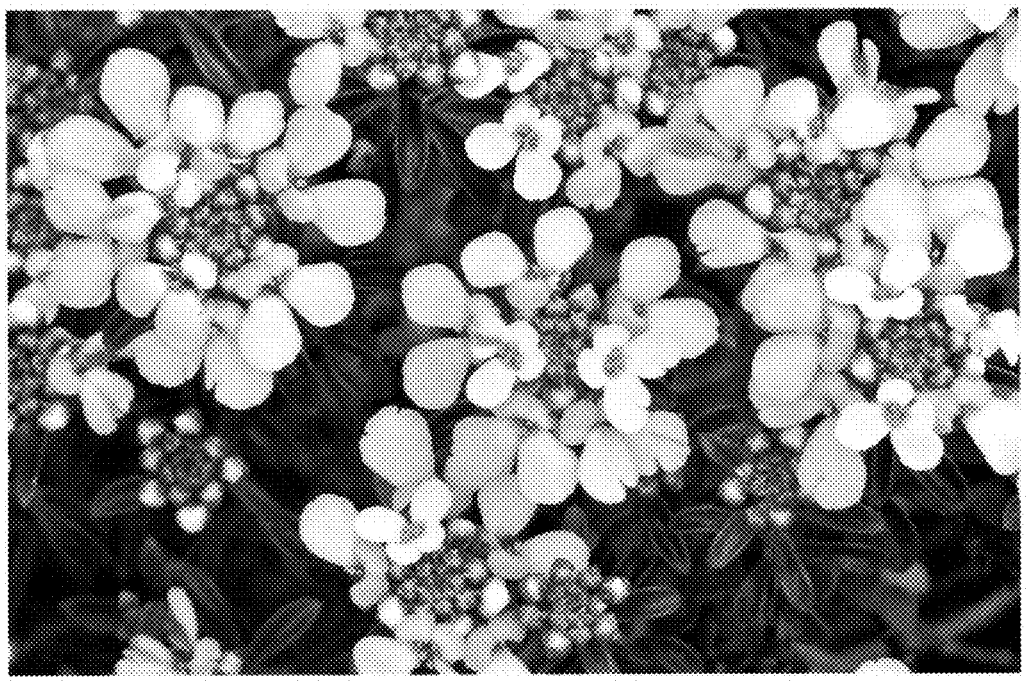

The photograph in FIG. 2 provides a close-up view of the flowers of 'Pink Ice'.

The color values cited in the detailed botanical description accurately describe the colors of the new *Iberis*.

DETAILED BOTANICAL DESCRIPTION

The following is a detailed description of a plant about 8 months in age of the new cultivar as grown outdoors in a 2-gallon container in Watsonville, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early May to mid July in the United Kingdom.

*Plant habit.*—Herbaceous perennial, densely branched and compact.

*Height and spread.*—Matures to about 30 cm in height and about 20 cm in width.

*Hardiness.*—At least to 10° F. in the U.K.

*Diseases and pests.*—No susceptibility or resistance has been observed.

*Root description.*—Fibrous.

Growth and propagation:

*Propagation.*—Stem cuttings.

*Growth rate.*—Moderate.

Stem description:

*Stem strength.*—Strong and held upright.

*Shape.*—Round with ridges.

*Stem color.*—Wood base; a blend of 161A and 165A, new stems; ridges of 144A and 144B.

*Stem size.*—Lateral; an average of 2.5 mm in diameter and 20 cm in length secondary; an average of 2 mm in diameter and 15 cm in length, tertiary; an average of 2 mm in diameter and 7 cm in length, all lengths including peduncles.

*Stem surface.*—Ridged and moderately pubescent.

*Branching habit.*—Numerous branches emerge from woody base, an average of 50 lateral branches, 7 secondary branches per lateral branch, 0 to 2 tertiary branches per secondary branch in a 2-gallon container.

Foliage description:

*Leaf division.*—Simple.

*Leaf shape.*—Spatulate.

*Leaf base.*—Blunt, clasping to stem.

*Leaf apex.*—Broadly acute.

*Leaf margin.*—Entire, sparsely pubescent.

*Leaf venation.*—Not discernable.

*Leaf attachment.*—Sessile.

*Leaf arrangement.*—Whorled.

*Leaf surface.*—Glandular and glossy on upper and lower surfaces.

*Leaf color.*—Newly emerged and mature upper surface; 137A, newly emerged and mature lower surface; 137B.

*Leaf aspect.*—Slightly recurved.

*Leaf size.*—An average of 2.2 cm in length and 5 mm in width.

*Foliage fragrance.*—None.

Flower description:

General description:

*Type.*—Rounded raceme.

*Lastingness of inflorescence.*—About 3 weeks on the plant.

*Fragrance.*—Slightly pungent.

*Quantity of inflorescences.*—One per terminal, secondary and tertiary stems, about 500 in a 2-gallon container.

*Inflorescence size.*—An average of 3 cm in diameter and 1.5 cm in depth.

*Flower type.*—Polysymetric with 2 smaller adaxial petals and 2 larger abaxial petals.

*Flower size.*—About 9 mm in diameter and 6 mm in depth.

*Flower number.*—Average of 26 per corymbs.

*Flower buds.*—About 3 mm in height and diameter, globose in shape, color 60 C to 60D in color with apex NN155D and sepal portion 144B.

*Peduncle.*—Primary an average of 4 cm in length and 2.5 mm in diameter with laterals an average of 4.5 cm in length and 2 mm in width, color; ridges of 144A and 144B, surface is moderately pubescent.

*Pedicels.*—An average of 5 mm in length and 1 mm in diameter, 144B in color, surface is moderately pubescent.

*Petals.*—4, 2 adaxial and 2 abaxial, adaxial; limb strongly reflexed, limb is orbicular in shape, glabrous surface, rounded apex, margins entire, limb is about 4 mm in width and length, claw is about 2 mm in length and 0.5 mm in width with truncate base, color upper and lower surfaces: newly opened flower; NN155D, color on fully open flower; a blend of 76C, 84C and NN155D, abaxial; limb held outward, rotund in shape, glabrous surface, rounded apex, margins entire, limb is about 6 mm in width and 5 mm in length, claw is about 2.5 mm in length and 1 mm in width with truncate base, color upper and lower surfaces: newly opened flower; NN155D, color on fully open flower; a blend of 76C, 84C and NN155D.

*Calyx.*—Open campanulate in form, 3 mm in height and 4 mm in width.

*Sepals.*—4, un-fused, oblong in shape, an average of 3 mm in length and 1.5 mm in width, acute apex, truncate base, glabrous on outer and inner surfaces, color of outer and inner surface; margins N155D, centers 144B.

Reproductive organs:

*Gynoecium.*—Pistil; 1, style; 144B in color, crystalline in appearance, about 6 mm in length and <1 mm in width, stigma; minute, globose, 144A in color, ovary; superior, rounded oblong in shape with 2 pointed apex and style running through it, 2.5 mm in length and 2 mm width, 144C in color.

*Androcoecium.*—Stamens; 4, un-fused, filament; N145D in color, about 5 mm in length, crystalline in appearance, anther; 161B in color, dorsifixed, about 1.5 mm in length and 1 mm in width, pollen; moderate in quantity and 162A in color.

*Fruit and seed.*—Not observed under the conditions tested.

It is claimed:

1. A new and distinct cultivar of *Iberis* plant named 'Pink Ice' as herein illustrated and described.

* * * * *